United States Patent [19]

Vo-Dinh

[11] Patent Number: 4,680,165

[45] Date of Patent: Jul. 14, 1987

[54] DOSIMETER FOR MONITORING VAPORS AND AEROSOLS OF ORGANIC COMPOUNDS

[76] Inventor: Tuan Vo-Dinh, 625 Gulfwood Rd., Knoxville, Tenn. 37923

[21] Appl. No.: 359,791

[22] Filed: Mar. 19, 1982

[51] Int. Cl.[4] ............................................. G01N 31/00
[52] U.S. Cl. ........................................ 422/88; 436/91; 436/902
[58] Field of Search .................. 422/58, 61, 83, 86, 422/87, 88; 436/901

[56] References Cited

U.S. PATENT DOCUMENTS

| | | | |
|---|---|---|---|
| 3,901,657 | 8/1975 | Lightfoot | 436/901 X |
| 3,950,980 | 4/1976 | Braun et al. | 422/83 X |
| 3,985,017 | 10/1976 | Goldsmith | 422/83 X |
| 4,256,694 | 3/1981 | McAllister et al. | 422/58 |
| 4,272,480 | 6/1981 | Stull et al. | 422/86 X |
| 4,327,575 | 5/1982 | Locker | 73/23 |

FOREIGN PATENT DOCUMENTS 1075054  7/1967  United Kingdom .

OTHER PUBLICATIONS

Applied Spectroscopy Reviews, 13(2), 261–294 (1977), "Room Temperature Phosphorimetry as a New Spectrochemical Method of Analysis" by T. Vo Dinh and J. D. Winefordner.
Short Communications—"Room-Temperature Phosphorence of Several Polyaromatic Hydrocarbons" by T. Vo Dinh, E. Lue Yen and J. D. Winefordner.
Analytical Chemistry, vol. 51, p. 1915, Oct. 1979—"Selective Heavy-Atom Perturbation for Analysis of Complex Mixtures by Room-Temperature Phosphorimetry" by T. Vo-Dinh and J. R. Hooyman.

Primary Examiner—Barry S. Richman
Assistant Examiner—Michael S. Gzybowski
Attorney, Agent, or Firm—Luedeka & Neely

[57] ABSTRACT

A dosimeter is provided for collecting and detecting vapors and aerosols of organic compounds. The dosimeter comprises a lightweight, passive device that can be conveniently worn by a person as a badge or placed at a stationary location. The dosimeter includes a sample collector comprising a porous web treated with a chemical for inducing molecular displacement and enhancing phosphorescence. Compounds are collected onto the web by molecular diffusion. The web also serves as the sample medium for detecting the compounds by a room temperature phosphorescence technique.

2 Claims, 7 Drawing Figures

DOSIMETER FOR MONITORING VAPORS AND AEROSOLS OF ORGANIC COMPOUNDS

The U.S. Government has rights in this invention pursuant to Contract No. W-7405-ENG-26 awarded by the U.S. Department of Energy.

The present invention relates generally to monitors of vapors and aerosols of organic compounds and, more specifically, to a passive dosimeter designed for sampling vapors and aerosols of organic chemicals such as the polynuclear aromatic (PNA) compounds onto a porous solid surface, such as a chemically treated paper, and detecting these PNA species directly on the solid surface by room temperature phosphorescence technique.

Inhalation of vapors and aerosols of polynuclear aromatic compounds is one of the major health hazards in many workplace and residential environments. The PNA compounds are multi-ring benzenoid (two-ring and up) molecules produced in many industrial and residential activities, for example, liquefaction or gasification of coal, burning of organic materials, etc. Many of these compounds are known to be carcinogenic.

Presently there are various instruments capable of locating and identifying surfaces contaminated with PNAs. These include a spill spotter and a luminoscope for detecting fluorescing materials on the skin and the like. Traditional air monitoring methods include drawing air through solid sorbent materials for long periods of time. Subsequently the PNAs are thermally desorbed or chemically extracted from the sorbent materials, then analyzed, generally by chromatography. Several passive dosimeters have been reported to measure vapors of organic compounds in ambient air. The organic molecules trapped onto the solid sorbents of prior passive dosimeters must be extracted or desorbed from the sorbent and analyzed in another sample medium. Desorption and extraction both involve elaborate, costly, and time-consuming procedures.

It is, accordingly, an object of the present invention to provide a passive dosimeter for organic vapors and aerosols. It is another object to provide a dosimeter capable of performing both vapor and aerosol sample collection and detection by room temperature phosphorescence (RTP) analysis on a single device. Another object of the present invention is to provide a device that can monitor vapors from compounds including polynuclear aromatic compounds directly without the need of extraction and desorption of the collected substance from the collection medium.

In accordance with the present invention, a compact, badge-size dosimeter is provided for in situ collection of vapors and aerosols of organic compounds by molecular diffusion and for detecting these species by spectroscopic measurement, e.g., room temperature phosphorescence (RTP).

Simplicity, rapidity, and cost-effectiveness of operation result from the dual ability to passively collect and analyze on the same sample medium. The compact size and light weight of the dosimeter of the present invention makes it easy to be worn by a person or placed in a stationary location.

Various other objects and advantages will be apparent when the following description is considered in connection with the accompanying drawings in which.

Generally, in accordance with the present invention, a passive dosimeter is provided for monitoring the level of organic compounds, such as polynuclear aromatics, in the environment surrounding the dosimeter. The dosimeter includes a base and a diffusion chamber is secured to the base and extends outwardly from the base to define an outer end and an inner end to the chamber. A porous web, carrying one or more chemicals on at least the exterior surface, is secured in spaced relation to the outer end of the diffusion chamber. The particular chemical is adapted to induce molecular displacement and enhance phosphorescence of said vapors and aerosols and is selected in accordance with the specific organic compound or compounds being monitored.

The chemical on the exterior surface of the porous web induces the monitored compound to diffuse into the porous web, thus maintaining a low concentration of the compound at the exterior surface. After a selected period of time, the porous web is analyzed by room temperature phosphorescence techniques to measure the collection of the selected organic compound.

Figure 1:
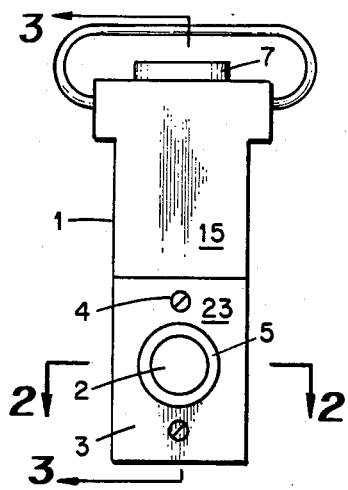
FIG. 1 is a front elevational view of a dosimeter embodying various of the features of the present invention.
Figure 3:
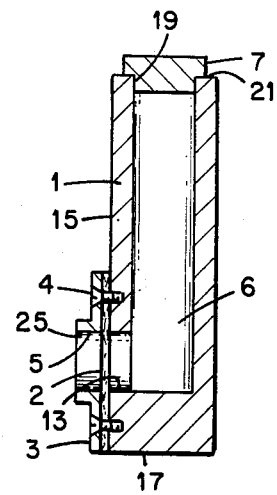
FIG. 3 is a cross-sectional view taken along line 3—3 of FIG. 1.
Figure 2:
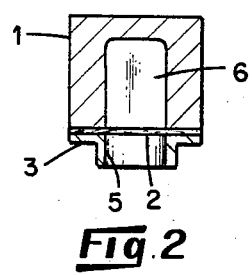
FIG. 2 is a cross-sectional view taken along line 2—2 of FIG. 1.

Referring more specifically to the drawings, initially to FIGS. 1, 2 and 3, one embodiment of a dosimeter in accordance with the present invention is shown in front view, horizontal cross-section, and vertical cross-section, respectively. The dosimeter includes an elongated base 1 which may be fabricated from any lightweight, substantially rigid, material such as aluminum, teflon, or acrylic plastic. The base 1 is about 6 cm in length and about 2 cm in width and depth.

The base 1 defines an L-shaped bore 6 extending from a first aperture 13 defined in the face 15, adjacent a first end 17 of the base 1, to a second aperture 19 defined in the end wall 21. The second aperture 19 is closed by a cap 7.

The first aperture 13 is covered by a porous web 2 of filter paper. Suitable filter papers are available from Schleicher & Schuell of Keene, N.H., under product designations 2043A, 2040A or 59lc. Various other filter papers may be used as well. The web 2 is maintained in a fixed position, covering the aperture 13, by a collar 3 including a cylindrical ring 5 defining a tubular diffusion chamber and a peripheral shoulder 23. The ring 5 is about 0.5 cm in length and has a diameter of about 0.5 to 0.7 cm, equivalent to the diameter of the bore 6. The collar 3, comprising a material similar to that of the base 1, is secured to the base 1 with two screws 4 extending through the collar 3, with the ring 5 in register with the bore 6.

The paper web 2 is treated with one or more chemicals selected to aid in the collection and analysis of the particular organic compounds being monitored. Polynuclear aromatic compounds are activated for room temperature phosphorescence by several heavy atom compounds, such as lead acetate, thallium acetate, sodium iodide, sodium bromide, silver nitrate, cesium iodide and lithium chloride, nickel chloride, lanthanum nitrate, barium nitrate, strontium chloride, sodium chloride, manganese chloride, cupric nitrate, cobalt chloride, lead nitrate, calcium carbonate, mercuric iodide, and barium hydroxide. For example, phenanthrene is perturbed for room temperature phosphorescence by thallium acetate, $AgNO_3$ and NaI. Benzo [a] pyrene is perturbed well by lead acetate. Pyrene is perturbed well with $AgNO_3$. Carbazole responds well to NaOH and NaI. Generally speaking, NaI is an efficient perturber for heterocyclic and ionic compounds and $AgNO_3$ is specifically efficient for polynuclear aromatic compounds. Lead acetate and thallium acetate are also efficient perturbers for other polynuclear aromatic compounds.

Figure 4:
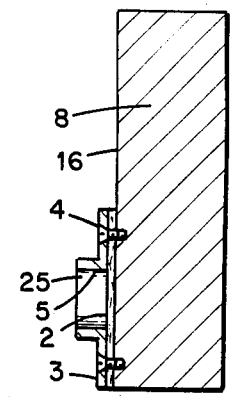
FIG. 4 is a cross-sectional view, similar to FIG. 3, of an alternative embodiment of a dosimeter embodying various features of the present invention.

FIG. 4 illustrates an embodiment of a dosimeter in which the base 8 is solid, defining no central bore. The web 2 is mounted directly to the face 16 of the base 8, secured in position by the collar 3 as in the embodiment depicted in FIGS. 1, 2 and 3.

Figure 5:
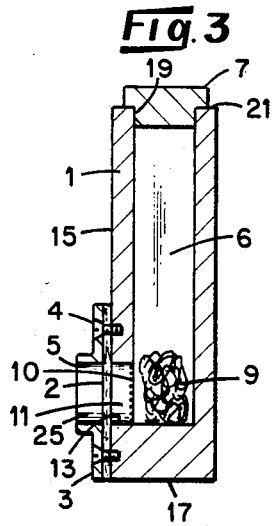
FIG. 5 is a cross-sectional view, similar to FIG. 3 of an alternative embodiment of a dosimeter embodying various of the features of the present invention.

FIG. 5 illustrates an alternative dosimeter embodiment wherein the bore 6 contains an additional sorbent material 9 such as activated charcoal, silicagel, or a porous polymer material. In the embodiment of FIG. 5, the sorbent material 9 is restrained within the bore 6 by a grid 10 in spaced relation with the web 2. Thus, a diffusional space 11 is defined between the web 2 and the sorbent material 9.

Figure 6:
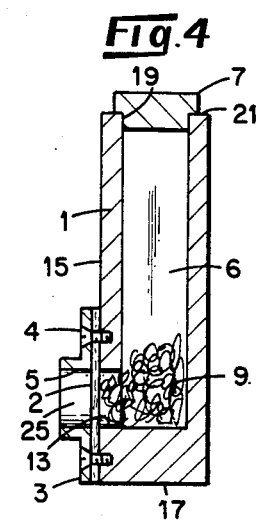
FIG. 6 is a cross-sectional view, similar to FIG. 3 of an alternative embodiment of a dosimeter embodying various of the features of the present invention; and, FIG. 7 is a perspective view of the dosimeter of FIG. 1.
Figure 7:
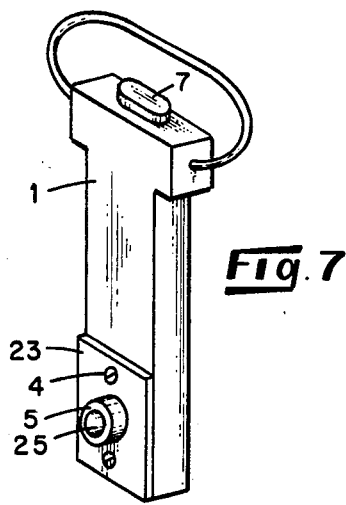

FIG. 6 illustrates another alternative dosimeter embodiment wherein the additional sorbent material 9 extends within the bore 6 up to contact with the interior surface of the web 2.

The vapor and aerosol collection technique employed in the present invention generally employs the principle of molecular diffusion. The dosimeter is secured to a person's clothing, as with a clip, for example, or at a fixed location in the environment being monitored. During sampling, the treated surface of the web 2 is exposed to the environment to be measured through the diffusion chamber. The chemical with which the web is treated has the dual purpose of increasing adsorptivity of the porous web, such as filter paper, and enhancing the phosphorescent emission of the polynuclear aromatic molecules collected on the web. The treated web keeps the concentration of the collected compounds nearly zero at the treated exterior surface while the open end 25 of the diffusion chamber is at the ambient concentration. This sets up a concentration gradient along the diffusion chamber for diffusion of the collected molecules from the outside of the dosimeter to the web 2. This concentration gradient provides the driving force to move the vapors onto the paper web, eliminating the need for a pump.

The transfer of vapors by diffusion is described by Fick's first law:

$$J = -D\frac{dc}{dl}$$

where
D = coefficient of diffusion of the PNA compound ($cm^2$/sec)
J = diffusion flux (moles/$cm^2$/sec)
c = concentration (moles/$cm^3$)
l = length of diffusion path (cm)

For some situations, it is desirable to increase the adsorptivity of the web and/or the diffusion rate by using an additional sorbent material placed behind the filter paper. This mode of use is shown in the embodiments depicted in FIGS. 5 and 6. The monitored compounds are moved into and trapped upon the web 2. For the collection of some compounds, the sorbent material 9 is supplied with a solvent, such as ethanol or water or an acidic or basic liquid in order to further increase the diffusion rate of the monitored compound and/or improve the adsorptivity of the web material.

After a selected period of monitoring, which may be predetermined or following an exposure to a chemical, the identity and level of organic compounds adsorbed on the web are then determined directly by the technique of room temperature phosphorescence.

The foregoing description of the invention is offered for illustrative purposes only and should not be interpreted in a limiting sense. It will be recognized, for example, that other types of diffusional chamber having different configuration or equipped with an external grid or membrane, may be used. Different shapes of dosimeters may also be contructed. In addition, porous webs other than filter paper, such as silica gel or polymer materials, may be used as sample medium for room temperature analysis. The collection surface may also have a geometrical configuration other than circular and carry a plurality of chemicals adapted to increase diffusion and/or enhance phosphorescence.

While a preferred embodiment has been shown and described herein, it will be understood that there is no intent to limit the invention by such disclosure, but rather, it is intended to cover all modifications falling within the spirit and scope of the invention as defined in the appended claims.

What is claimed:

1. A dosimeter for in situ collection and direct detection of vapors and aerosols of polynuclear aromatic compounds by room temperature phosphorimetry comprising a base, a diffusion chamber secured to and extending outwardly from said base to define an open outer end of said chamber and an inner end of said chamber adjacent to said base, said base defining a bore terminating in register with said diffusion chamber and said bore containing a sorbent material and a grid whereby said sorbent material is maintained in spaced relation with filter paper which contains a heavy atom compound to collect said vapors and aerosols of polynuclear aromatic compounds by absorption, said filter paper having an exterior surface and being secured to said base adjacent to said inner end of said diffusion chamber with said exterior surface of said filter paper having exposure to said diffusion chamber, whereby, said heavy atom compound on said filter paper increases the absorptivity of said filter paper for said vapors and aerosols of polynuclear aromatic compounds during collection and enhances phosphorescence emission of said collected polynuclear aromatic compounds on said filter paper during detection, the dosimeter further comprising a solvent supplied to said sorbent material for improving the absorptivity of said filter paper containing a heavy atom compound.

2. The dosimeter of claim 1 wherein said solvent is selected from the group consisting of water, ethanol, acidic liquids, and basic liquids.

* * * * *